United States Patent
Brutto et al.

(10) Patent No.: US 8,697,754 B2
(45) Date of Patent: *Apr. 15, 2014

(54) AMINOALCOHOL AND BIOCIDE COMPOSITIONS FOR AQUEOUS BASED SYSTEMS

(75) Inventors: Patrick E. Brutto, Bloomingdale, IL (US); Charles E. Coburn, Vernon Hills, IL (US); G. David Green, Cary, IL (US); Bonnie A. Pyzowski, Park Ridge, IL (US); Raymond J. Swedo, Mt. Prospect, IL (US); John Pohlman, Skokie, IL (US)

(73) Assignees: Dow Global Technologies LLC; ANGUS Chemical Company

( * ) Notice: Subject to any disclaimer, the term of this patent is extended or adjusted under 35 U.S.C. 154(b) by 306 days.

This patent is subject to a terminal disclaimer.

(21) Appl. No.: 12/988,404

(22) PCT Filed: Apr. 29, 2009

(86) PCT No.: PCT/US2009/042032
§ 371 (c)(1),
(2), (4) Date: Oct. 18, 2010

(87) PCT Pub. No.: WO2009/140061
PCT Pub. Date: Nov. 19, 2009

(65) Prior Publication Data
US 2011/0046140 A1 Feb. 24, 2011

Related U.S. Application Data

(60) Provisional application No. 61/053,408, filed on May 15, 2008, provisional application No. 61/073,894, filed on Jun. 19, 2008.

(51) Int. Cl.
| | |
|---|---|
| A01N 33/08 | (2006.01) |
| A01N 43/64 | (2006.01) |
| A01N 43/80 | (2006.01) |
| A61K 31/53 | (2006.01) |
| A61K 31/133 | (2006.01) |
| A61K 31/428 | (2006.01) |
| C10L 1/222 | (2006.01) |
| C10M 133/08 | (2006.01) |
| C09D 5/14 | (2006.01) |
| C11D 3/26 | (2006.01) |
| C11D 3/48 | (2006.01) |
| C11D 9/30 | (2006.01) |
| C11D 9/50 | (2006.01) |

(52) U.S. Cl.
USPC ........... 514/667; 514/241; 514/373; 508/551; 508/562; 106/18.32; 106/18.33; 510/382; 510/389; 507/130; 507/131; 507/242; 507/244

(58) Field of Classification Search
USPC .......... 514/241, 373, 667; 507/131, 130, 242, 507/244; 508/551, 562; 106/18.33, 18.32; 510/389
See application file for complete search history.

(56) References Cited

U.S. PATENT DOCUMENTS

| | | | |
|---|---|---|---|
| 2,164,271 A | 6/1939 | Hass et al. | |
| 2,695,222 A * | 11/1954 | Chenicek et al. | 44/434 |
| 3,247,054 A | 4/1966 | Hodge et al. | |
| 4,074,013 A | 2/1978 | Koch et al. | |
| 4,166,725 A | 9/1979 | Amick | |
| 4,708,720 A | 11/1987 | Grangette et al. | |
| 4,877,552 A | 10/1989 | Haring | |
| 4,925,582 A * | 5/1990 | Bennett | 508/248 |
| 5,154,817 A | 10/1992 | Reid | |
| 6,267,791 B1 | 7/2001 | Thomas et al. | |
| 6,607,566 B1 | 8/2003 | Coleman et al. | |
| 2003/0027889 A1 | 2/2003 | Inhester et al. | |
| 2003/0162845 A1 | 8/2003 | O'Reilly et al. | |
| 2003/0209165 A1 | 11/2003 | Gernon | |
| 2005/0266235 A1 * | 12/2005 | Nakajima et al. | 428/336 |
| 2010/0242341 A1 | 9/2010 | Tinetti et al. | |
| 2011/0028732 A1 * | 2/2011 | Trauth et al. | 548/215 |

FOREIGN PATENT DOCUMENTS

| | | |
|---|---|---|
| JP | 6-92806 | 4/1994 |
| JP | 08193015 | 7/1996 |
| WO | 9117746 | 11/1991 |
| WO | WO 9315173 A1 * | 8/1993 |
| WO | 9412028 | 6/1994 |
| WO | WO 9604274 A1 * | 2/1996 |
| WO | 2004057964 | 7/2004 |

(Continued)

OTHER PUBLICATIONS

Gereon Altenhoff, Richard Goddard, Christian W. Lehmann, and Frank Glorius, Sterically Demanding, Bioxazoline-Derived N-Heterocyclic Carbene Ligands with Restricted Flexibility for Catalysis, J. Am. Chem. Soc. 2004, 126, 15195-1520.*

(Continued)

Primary Examiner — Kendra D Carter
Assistant Examiner — Jason A Desk (57) ABSTRACT

Biocidal compositions and their use in aqueous media, such as metalworking fluids, the compositions comprising a biocidal agent; and a non-biocidal primary amino alcohol compound of the formula (I): wherein $R^1$, $R^2$, $R^3$, $R^4$, and $R^5$ are as defined herein.

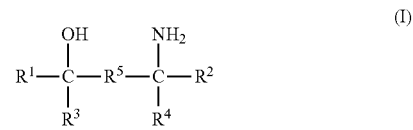

14 Claims, 6 Drawing Sheets

(56) References Cited

FOREIGN PATENT DOCUMENTS

| WO | 2006016991 | 2/2006 |
| WO | 2007018782 | 2/2007 |
| WO | 2007032918 | 3/2007 |
| WO | WO 2008/088632 A2 * | 12/2007 |
| WO | 2008088632 | 7/2008 |
| WO | 2009140062 | 11/2009 |
| WO | WO 2009140062 A1 * | 11/2009 |

OTHER PUBLICATIONS

Gereon Altenhoff, Richard Goddard, Christian W. Lehmann, and Frank Glorius, Sterically Demanding, Bioxazoline-Derived N-Heterocyclic Carbene Ligands with Restricted Flexibility for Catalysis, J. Am. Chem. Soc. 2004, 126, 15195-1520; supplemental information.*

NOLAND, Derivatives of (1-Aminocyclohexyl)methanol, Nov. 26, 1956, pp. 695-697.

Aitken et al., "Studies on the Condensation Products from N-Primary 1,2-Amino Alcohols and Formaldehyde", Heterocycles, 2004, vol. 64, pp. 277-289.

Borrows et al., "Preparation and Properties, etc: Preparation and Properties of Some Long-Chain Aliphatic Amines", 1947, pp. 197-202, Chapter 47.

Brutto et al., "Some Key Building Blocks for Long-Life Bioresistant Metalworking Fluids", Powerpoint Presentation at STLE Annual Meeting, 2005.

Gernon, "Arkema and Metalworking", Arkema Inc., Tribology & Lubrication Technology 2005, pp. 38-40, vol. 61 No. 11.

Kubis et al., "Investigation on Antibacterial Action of Some Amines", Pharmazie, 1983, pp. 488-489, vol. 38, H. 7.

MacLeod et al., "Cation Antagonism of the Antibacterial Action of Amines", Inorganic Ions and Amine Toxicity, 1951, pp. 193-201.

Robbins et al., "A review of the microbiological degradation of fuel", Directory of Microbiocides for the Protection of Materials: A Handbook, 2005, pp. 177-202.

Sandin et al., "The role of alkyl chain length on the antibacterial activity of alkyl ethanolamines", Biomedical Letters, 1992, pp. 85-92, vol. 47, The Faculty Press.

"An Outstanding Multi-functional Amine Additive for Metalworking Fluids", Synergex Premier published prior to May 2007.

Database WPI Week 199640, Thomson Scientific, London GB; AN 1996-397196 XP002509608 & JP 08193015 abstract.

Database WPI Week 199640 Thomson Scientific, London, GB AN 1996-397196 XP002516784.

"Metalworking Fluid Additives" ANGUS Chemical Company, 2003.

Reason for Rejection from Japanese Patent Application No. 2011-509540 dated Sep. 12, 2013.

* cited by examiner

Fig. 5: Bacterial Control - Semi-Synthetic MWF with Benzisothiazolone (3000 ppm Amine)

Fig. 6: Fungal Control - Semi-Synthetic MWF with Benzisothiazolone (3000 ppm Amine)

AMINOALCOHOL AND BIOCIDE COMPOSITIONS FOR AQUEOUS BASED SYSTEMS

CROSS-REFERENCE TO PRIOR RELATED APPLICATIONS

This is a §371 application of PCT International Patent Application Number PCT/US2009/042032 filed Apr. 29, 2009, and claims priority from U.S. Provisional Application No. 61/053,408, filed May 15, 2008 and U.S. Provisional Application No. 61/073,894 filed Jun. 19, 2008, each of which is incorporated herein by reference in its entirety.

FIELD OF THE INVENTION

The invention relates to biocidal compositions for use in aqueous-based systems such as metalworking fluids, to methods of use, and to novel amino alcohol compounds.

BACKGROUND OF THE INVENTION

Short chain amino alcohols are used commercially in a wide variety of applications because of their anti-corrosion, neutralization and pH adjustment and maintenance properties. One such application is in metalworking fluids.

Metalworking fluids ("MWFs") are used throughout the manufacturing industry for their coolant, lubricant, and corrosion resistant properties during operations such as metal cutting, grinding, boring, drilling, and turning. These fluids are made of mixtures of oils, detergents, surfactants, lubricants, anti-corrosion agents, water and other ingredients, and usually contain amino alcohols for maintaining alkaline pH and for neutralizing acid functional components in the MWFs.

Companies producing and using water-miscible MWFs want them to last a long time in order to minimize operating and waste disposal costs as well as loss of production time. Water-miscible MWFs containing amino alcohols as corrosion inhibitors are degraded over time by processes such as microbial degradation. Microbial growth is often directly related to fluid performance because microbes feed on the active ingredients in the fluid.

An industry need exists for amino alcohol components which do not support microbial growth and which maintain performance over a long time period. A need also exists for amino alcohols which, although not biocidal themselves, enhance the performance of a wide range of biocides used in water-based MWFs. While secondary amines are in common use, primary amines that fulfill the above purposes would be desirable because of regulatory restrictions on use of secondary amines in certain parts of the world.

The present invention addresses the above-described needs.

BRIEF SUMMARY OF THE INVENTION

In one aspect, the invention provides a biocidal composition. The composition comprises a biocidal agent and a primary amino alcohol compound that is non-biocidal, wherein the primary amino alcohol compound is of the formula (I):

wherein $R^1$, $R^2$, $R^3$, $R^4$, and $R^5$ are as defined below.

In another aspect, the invention provides aqueous-based systems (i.e. systems containing sufficient water to support microbial growth), such as metalworking fluids, comprising the biocidal compositions disclosed herein.

In another aspect, the invention provides a method of inhibiting the growth of microorganisms in an aqueous-based system comprising adding to said system an effective amount of a composition as described herein.

DETAILED DESCRIPTION OF THE INVENTION

The invention provides biocidal compositions comprising a biocide and an amino alcohol of formula (I), defined below, and their use for the inhibition of microorganism growth in aqueous based systems. The inventors have discovered that primary amino alcohols of formula (I), which contain at least 5 carbon atoms, although themselves not biocidal, surprisingly enhance the performance of biocides used in various media. As a result, the invention permits for reduced use of biocides in various applications, thereby reducing material, transportation, and storage costs.

The biocidal agent (also referred to herein as "biocide" or "preservative") is any substance that kills or inhibits the growth of microorganisms such as bacteria, molds, slimes, fungi, algae and the like, including formaldehyde based and non-formaldehyde based biocidal agents. Specific, non-limiting, examples of suitable agents include: tetrakis (hydroxymethyl) phosphonium sulfate (THPS) such as AQUCAR THPS 75 from The Dow Chemical Company, triazines such as 1,3,5-tris-(2-hydroxyethyl)-s-triazine and trimethyl-1,3,5-triazine-1,3,5-triethanol, an example being GROTAN by Troy Corporation, iodopropynylbutylcarbamate, such as POLYPHASE supplied by Troy Corporation, 1,2-benzisothiazolin-3-one, such as BIOBAN BIT marketed by The Dow Chemical Company, 4,4-dimethyloxazolidine, an example being BIOBAN CS-1135 from The Dow Chemical Company, 7-ethyl bicyclooxazolidine, marketed as BIOBAN CS-1246 by The Dow Chemical Co., a combination of 4-(2-nitrobutyl)-morpholine with 4,4'-(2-ethyl-2-nitrotrimethylene)dimorpholine, marketed as BIOBAN P-1487 by The Dow Chemical Co., 2-methyl-4-isothiazolin-3-one, a combination of 5-chloro-2-methyl-4-isothiazolin-3-one with 2-methyl-4-isothiazolin-3-one, such as the KATHON brand supplied by Rohm & Haas Corporation, 2-bromo-2-nitro-1,3-propanediol, octylisothiazolinone, dichloro-octylisothiazolinone, dibromooctylisothiazolinone, phenolics such as o-phenylphenol and p-chloro-m-cresol and their corresponding sodium and/or potassium salts, sodium pyrithione, zinc pyrithione, n-butyl benzisothiazolinone, 1-(3-chloroallyl)-3,5,7-triaza-1-azoniaadamantane chloride, chlorothalonil, carbendazim, diiodomethyltolylsulfone, 2,2-dibromo-3-nitrilopropionamide (DBNPA), glutaraldehyde, N,N'-Methylene-bis-morpholine, ethylenedioxy methanol (e.g. Troyshield B7), phenoxyethanol, (e.g. Comtram 121), tetramethylol acetylenediurea (e.g. Protectol TD), dithiocarbamates, 2,6-Dimethyl-m-dioxan-4-ol acetate (e.g Bioban DXN), dimethylol-dimethyl-hydantoin, tris(hydroxymethyl) nitromethane, bicyclic oxazolidines (e.g. Nuospet 95), and mixtures of two or more thereof. In the invention, non-formaldehyde agents are preferred because of industry preference in developed countries, however, one of the advantages of the invention is that it is applicable to a wide variety of biocides.

Particularly preferred biocides are triazines, substituted oxazolidines, benzisothiazolinone, iodopropynylbutylcarbamate, sodium pyrithione, octylisothiazolinone, a combination of 5-chloro-2-methyl-4-isothiazolin-3-one with 2-methyl-4-isothiazolin-3-one, phenolics, glutaraldehyde, 2,2-dibromo-3-nitrilopropionamide (DBNPA), 1-(3-chloroallyl)-3,5,7-triaza-1-azoniaadamantane chloride, N,N'-Methylene-bis-morpholine, tetrakis(hydroxymethyl) phosphonium sulfate (THPS) such as AQUCAR THPS 75 from The Dow Chemical Company, and mixtures of two or more thereof.

The primary amino alcohol compound is of the formula (I):

(I)

wherein $R^1$ and $R^3$ are each independently H, linear or branched alkyl, alkenyl, alkynyl, cycloalkyl, or aryl (preferably phenyl), or $R^1$, $R^3$ and the carbon to which they are attached form a cycloalkyl ring, $R^2$ and $R^4$ are each independently H, linear or branched alkyl, cycloalkyl, cycloalkyl-alkyl, aryl, aryl-alkyl, or R2, R4 and the carbon to which they are attached form a cycloalkyl ring, provided that $R^2$ and $R^4$ together contain 3 or more carbon atoms; and $R^5$ is absent or is a $C_1$-$C_{10}$ aliphatic alkylene (bridging alkyl), arylene (preferably phenyl), -arylene-alkylene-, or -alkylene-arylene- (e.g., benzyl, phenethyl, and the like); wherein alkyl, cycloalkyl, alkylene, aryl, and arylene are optionally substituted with alkyl or phenyl. The compound of formula (I) contains at least 5 carbon atoms. In some embodiments, the compounds contains at least 6 carbon atoms. In further preferred embodiments, the compound contains no more than 13 carbon atoms. The aminoalcohol may be in the form of a mixture of two or more compounds of formula (I).

Preferred aminoalcohols of formula I include compounds of formula (II):

(II)

wherein $R^2$ and $R^4$ are each independently H, linear or branched alkyl, cycloalkyl, cycloalkyl-alkyl, aryl, aryl-alkyl or $R^2$, $R^4$ and the carbon to which they are attached form a cycloalkyl ring, and $R^2$ and $R^4$ together contain a total of at least 3 carbon atoms.

Preferred aminoalcohols of formula (II) include compounds of formula (II-1), which are compounds of formula (II) in which $R^2$ and $R^4$ together contain a total of up toll carbon atoms.

Preferred aminoalcohols of formula (II) and formula (II-1) include compounds of formula (II-2), which are compounds of formula (II) or (II-1) in which $R^2$ and $R^4$ are each independently linear alkyl.

Preferred aminoalcohols of formula (II) and formula (II-1) also include compounds of formula (II-3), which are compounds of formula (II) or (II-1) in which one of $R^2$ and $R^4$ is H and the other is linear alkyl.

Preferred aminoalcohols of formula (II) and formula (II-1) include compounds of formula (II-4), which are compounds of formula (II) or (II-1) in which $R^2$ and $R^4$ together with the carbon to which they are attached form a cycloalkyl ring.

Preferred aminoalcohols of formula (II) and formula (II-1) include compounds of formula (II-5), which are compounds of formula (II) or (II-1) in which one of $R^2$ and $R^4$ is $CH_3$ and the other aryl, preferably phenyl.

Preferred primary amino alcohols for use in the invention include, but are not limited to: 2-amino-2-methyl-1-hexanol, 2-amino-2-ethyl-1-pentanol, 2-amino-2-methyl-1-heptanol, 2-amino-2-ethyl-1-hexanol, 2-amino-2-propyl-1-pentanol, 2-amino-2-methyl-1-octanol, 2-amino-2-ethyl-1-heptanol, 2-amino-2-propyl-1-hexanol, 2-amino-2-methyl-1-nonanol, 2-amino-2-ethyl-1-octanol, 2-amino-2-propyl-1-heptanol, 2-amino-2-butyl-1-hexanol, 2-amino-2-methyl-1-decanol, 2-amino-2-ethyl-1-nonanol, 2-amino-2-propyl-1-octanol, 2-amino-2-butyl-1-heptanol, 2-amino-2-methyl-1-undecanol, 2-amino-2-ethyl-1-decanol, 2-amino-2-propyl-1-nonanol, 2-amino-2-butyl-1-octanol, 2-amino-2-pentyl-1-heptanol, 2-amino-2-methyl-1-dodecanol, 2-amino-2-ethyl-1-undecanol, 2-amino-2-propyl-1-decanol, 2-amino-2-butyl-1-nonanol, 2-amino-2-pentyl-1-octanol, (1-aminocyclopentyl)methanol, (1-aminocyclohexyl)methanol, (1-aminocycloheptyl)methanol, (1-aminocyclooctyl) methanol, (1-aminocyclononyl)methanol, (1-aminocyclodecyl)methanol, (1-aminocycloundecyl)methanol, (1-aminocyclododecyl)methanol, 2-amino-2-phenyl-1-ethanol, 2-amino-2-phenyl-1-propanol, 2-amino-2-phenyl-1-butanol, and mixtures thereof.

Particularly preferred amino alcohols include: 2-amino-2-methyl-1-hexanol, 2-amino-2-ethyl-1-pentanol, 2-amino-2-methyl-1-octanol, 2-amino-2-ethyl-1-heptanol, 2-amino-2-propyl-1-hexanol, (1-aminocyclohexyl)methanol, (1-aminocyclooctyl)methanol, 2-amino-2-phenyl-1-propanol, (1-aminocyclopentyl)methanol, and mixtures thereof.

The amino alcohols may be used in the form of acid salts. Suitable salts include, but are not limited to, boric acid, lactic acid, pelargonic acid, nonanoic acid, neodecanoic acid, sebacic acid, azelaic acid, citric acid, benzoic acid, undecylenic acid, lauric acid, myristic acid, stearic acid, oleic acid, tall oil fatty acid, ethylenediaminetetraacetic acid and like materials.

The biocidal compositions may include additional additives, including, for instance other corrosion inhibitors, such as 2-amino-2-methyl-1-propanol (AMP), 2-amino-1-ethanol (MEA), 1-amino-2-propanol (MIPA), bis(2-hydroxypropyl)amine (DIPA), tris(2-hydroxypropyl)amine (TIPA), bis(2-hydroxyethyl)amine (DEA), tris(2-hydroxyethyl)amine (TEA), 2-(2-aminoethoxy)ethanol (DGA), 3-amino-4-octanol, or mixtures thereof. Less preferred of these additional additives are the secondary amines, because these are more heavily regulated in various parts of the world.

As noted above, the amino alcohols are not biocidal, i.e., they do not significantly inhibit biocidal growth. That is, at typical use levels (e.g., up to 4000 ppm in diluted MWF) these materials do not inhibit microbial growth to the extent of recognized biocidal agents intended for this purpose.

The amino alcohol compounds may be readily prepared by a person of ordinary skill in the art using techniques well known in the art. For example, such compounds may be prepared by the reaction of nitroalkanes with aliphatic or aromatic aldehydes or ketones or more preferably with formaldehyde, followed by catalytic hydrogenation.

The composition of the invention contains the amino alcohol compound and the biocide at various weight ratios, which will depend for instance on the particular biocide being used, and the particular aqueous medium. The ratio can be readily determined by a person of ordinary skill in the art. By way of a general example, the weight ratio of amino alcohol to biocide will generally be about 0.25:1 or greater and preferably about 500:1 or less. Further preferred amounts are described below.

As noted above, the compositions containing biocide of the invention are useful for inhibiting the growth of microorganisms in aqueous-based systems. Preferred systems for which the compositions of the invention are particularly suitable are metalworking fluids (MWFs). The compositions may be used with all types of MWFs, including soluble oil, synthetic, semi-synthetic, non-synthetic, emulsion forming, and non-emulsion forming fluids. Typically, MWFs are provided in a concentrated form and are diluted with water prior to use. The invention encompasses metalworking fluid concentrates containing the biocidal composition, diluted metalworking fluids thereof, metalworking fluid concentrates pre-diluted with water, as well as non-concentrate metalworking fluids to which the biocidal composition is added. Typically, 1 part by weight of a MWF concentrate is diluted with between about 10 and about 100 parts of water, more preferably 10 to 50 parts of water and most preferably with 15 to 30 parts of water.

Metalworking fluids and concentrates containing the biocidal compositions of the invention may contain hydrocarbon oils, which may be synthetic or non-synthetic. Examples of synthetic and non-synthetic oils commonly used include, for instance, mineral oils, vegetable oils, animal-derived oils, and synthetic polymers/copolymers. Specific examples of such oils include, without limitation, severely hydrotreated naphthenic and paraffinic oils, soybean oil and polyglycol block co-polymers.

Optional other additives well known in the art that may be included in the metalworking fluid (whether synthetic or non-synthetic) include, for example colorants; agents that alter viscosity; emulsifying agents (not generally required for synthetic MWFs because these are non-emulsion systems); buffers; solubilizers; anti-oxidants; anti-foaming agents; surfactants and antimisting agents and extreme pressure additives. The metalworking fluid will normally contain agents for inhibiting corrosion such as alkaline and amino alcohol salts (in addition to the compositions of the invention) of organic acids, sulfonates, amines, amides, and organic borate compounds.

By way of more specific example, emulsion-forming metalworking fluid concentrates, commonly known as soluble oils and semi-synthetics, typically contain the following types of components: Low viscosity hydrocarbon oils and synthetic lubricants such as polyalkylene glycols; Emulsifiers such as low molecular weight sodium petroleum sulfonates, alkanolamides, amine-fatty acid salts and non-ionic surfactants such as nonylphenol ethoxylates; Corrosion inhibitors such as medium-high molecular weight sodium petroleum sulfonates, alkanolamides, and amino alcohol salts of various organic and inorganic acids including nonanoic, neodecanoic, sebacic, oleic, tall oil, boric and many others; Coupling agents including glycol ethers and higher alcohols and glycols. Examples from each class include propylene glycol n-butylether, hexanol and hexylene glycol; and Lubricity and extreme pressure agents including fatty esters, phosphate esters, chlorinated fatty acids and sulfurized fatty acids By way of further example, non-emulsion forming metalworking fluid concentrates, commonly known as synthetic or solution synthetic fluids, typically contain the following: Lubricity and extreme pressure agents such as inversely soluble esters, phosphate esters, chlorinated fatty acids and polyalkylene glycols; Amine salts of organic and inorganic acids including pelargonic, neodecanoic, azelaic, dodecanoic, dodecanedioic, boric, lactic and many others. These materials are corrosion inhibitors.

The concentration of neat amino alcohol compound in the MWF concentrate (i.e., prior to dilution) is preferably at least about 1% by weight, more preferably at least about 2%, and even more preferably at least about 3%. Also preferably, the concentration is no more than about 20%, more preferably no more than about 12%, and even more preferably, no more than about 8%. In other embodiments, the concentration is in the range of about 1-20%, more preferably about 2-12%, and most preferably about 3-8%.

The preferred active concentration ranges for the biocide in the MWF concentrate varies depending on the biocide being used, but can be readily determined by a person of ordinary skill in the art. By way of example, the concentration is preferably at least about 0.01% by weight and no more than about 5% by weight.

By way of example for specific biocides, 1,3,5-tris(2-hydroxyethyl)-s-triazine is preferably used in the active range of 0.76 to 3% by weight, with a most preferred range of 1.1 to 3%, iodopropynylbutylcarbamate is used in the range of 0.2 to 0.6%, with a most preferred range of 0.3 to 0.6%, 1,2-benzisothiazolinone is used in the range of 0.08 to 0.36%, with a most preferred range of 0.16 to 0.36%, 4,4-dimethyloxazolidine is used in the range of 0.78 to 3.1% with a most preferred range of 1.2 to 3.1%, 7-ethyl bicycooxazolidine is used in the range 1 to 4% with a most preferred range of 1.5 to 4%, a combination of 4-(2-nitrobutyl)-morpholine with 4,4'-(2-ethyl-2-nitrotrimethylene)dimorpholine is used in the range of 1 to 4% with a most preferred range of 1.5 to 3%, and a combination of 5-chloro-2-methyl-4-isothiazolin-3-one with 2-methyl-4-isothiazolin-3-one is used in the range of 0.01% to 0.08% of with a most preferred range of 0.05% to 0.08%.

In the final diluted MWF, the use range of neat amino alcohol is preferably between about 0.05% to 1.0%, with a preferred range of 0.1% to 0.6%, and a most preferred range of 0.15% to 0.4%. The biocide agent is preferably used in the range (active basis at dilution) of 0.04% to 0.3% 1,3,5-tris (2-hydroxyethyl)-s-triazine with a preferred range of 0.06% to 0.15%, 0.01% to 0.04% iodopropynylbutylcarbamate with a preferred range of 0.015% to 0.03%, 0.004% to 0.03% 1,2-benzisothiazolin-3-one with a preferred range of 0.008% to 0.02%, 0.04% to 0.3% 4,4-dimethyloxazolidine with a preferred range of 0.06% to 0.2%, 0.05% to 0.3% 7-ethyl bicyclooxazolidine with a preferred range of 0.075% to 0.2%, 0.05% to 0.3% of a combination of 4-(2-nitrobutyl)-morpholine with 4,4'-(2-ethyl-2-nitrotrimethylene)dimorpholine with a preferred range of 0.075% to 0.2%, 0.002% to 0.005% of a combination of 5-chloro-2-methyl-4-isothiazolin-3-one with 2-methyl-4-isothiazolin-3-one with a preferred range of 0.0025% to 0.004%.

Although metalworking fluids are the preferred system in which the biocidal compositions of the invention are used, the compositions are also useful in a wide variety of other systems which contain water or are intended to be diluted with water. For instance, the compositions may be used in aqueous emulsions such as latexes, water-based paints & coatings, caulks and adhesives, tape joint compounds, mineral slurries, water-cooling systems, personal care products, soaps and detergents, disinfectants, cleaners, and sanitizers, pesticide products, oilfield water and water-based fluids used in oilfield applications including drilling muds, fracturing fluids, and hydrotest fluids, and the like.

"Alkyl," as used in this specification, encompasses straight and branched chain aliphatic groups having from 1-11 carbon atoms, more preferably 1-8 carbon atoms. Preferred alkyl groups include, without limitation, methyl, ethyl, propyl, isopropyl, butyl, isobutyl, sec-butyl, tert-butyl, pentyl, hexyl, heptyl, octyl, nonyl, decyl, and undecyl.

The term "alkenyl" as used herein means an unsaturated straight or branched chain aliphatic group with one or more carbon-carbon double bonds, having from 2-8 carbon atoms, and preferably 2-6 carbon atoms. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2-8 carbon atoms, and preferably 2-6 carbon atoms. Preferred alkynyl groups include, without limitation, ethynyl, propynyl, butynyl, pentynyl, and hexynyl.

An "alkylene" group is an alkyl as defined hereinabove, that is positioned between and serves to connect two other chemical groups. Preferred alkylene groups include, without limitation, methylene, ethylene, propylene, and butylene.

The term "cycloalkyl" as employed herein includes saturated and partially unsaturated cyclic hydrocarbon groups having 3 to 12 carbons, preferably 3 to 8 carbons. Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is a C6-C12 aromatic moiety comprising one to three aromatic rings. Preferably, the aryl group is a C6-C10 aryl group. Preferred aryl groups include, without limitation, phenyl, naphthyl, anthracenyl, and fluorenyl. More preferred is phenyl.

Alkyl, cycloalkyl, and aryl (and their bridging derivatives alkylene, cycloalkylene, and arylene) are optionally substituted with one or more other alkyl (e.g., methyl, ethyl, butyl), phenyl, or both. When substituted, the number of carbons in the substituent are counted towards the 5-13 carbons of the compound.

Non-limiting examples of the invention are provided in the below.

EXAMPLES

Example A

Preparation of 1-aminocyclohexylmethanol (AcyHM)

A 2-liter 3-neck flask equipped with a magnetic stirrer, nitrogen blanket, thermocouple controlled heating mantle and addition funnel is charged with nitrocyclohexane (521 g, 4.04 mol). Triethylamine catalyst (10.0 mL) is added and the yellow mixture warmed to 55° C. using the heating mantle. Via the addition funnel, aqueous formaldehyde (37% wt., 330 mL, 4.4 mol) is added dropwise over the period of 90 minutes. The reaction is very mildly exothermic, warming to 60° C. during the addition. After all the formaldehyde has been added, the reaction mixture is held at 60° C. for an additional 2 hours, poured into a separatory funnel and allowed to cool/phase separate overnight. The bottom, orange product layer is collected (750.8 g, contains dissolved water) and GC analysis indicates 96.9% purity with approximately 1.7% nitrocyclohexane and 1.4% triethylamine The product is used without further purification.

Catalytic hydrogenation of the 1-nitrocyclohexylmethanol to the 1-aminocyclohexylmethanol. A 2-liter Parr autoclave is charged with methanol (310 mL) and Raney Nickel catalyst (R-3111, 43.7 g wet weight). The reactor is sealed, purged with nitrogen followed by purging with hydrogen and then brought up to 65° C. under 500 psi hydrogen pressure. With rapid stirring, a solution of 1-nitrocyclohexylmethanol (4.04 mol actives containing about 105 g water) in methanol (800 mL total solution) is added over 3 hours while maintaining 65° C./500 psi hydrogen. When the addition is completed, the reaction is allowed to continue for an additional 20 minutes followed by cooling to room temperature. The autoclave is vented, opened and the crude product isolated via vacuum filtration. The methanol solvent is removed on a rotary evaporator at 50° C./29" vacuum. The yield of crude, stripped product is 755.6 g (still contains water). This is vacuum distilled through a fractionating column packed with stainless steel mesh, the product boiling between 85-86° C./15 torr is collected. GC analysis indicates >97% purity for the water white oil. The oil slowly crystallizes on standing. A final yield of 88% (459 g) of the purified product is obtained. The following amino alcohols are also prepared using the above procedure:

Example B

AhexM

A mixture (ratio is about 1 to 1) of 2-amino-2-methyl-1-hexanol and 2-amino-2-ethyl-1-pentanol is prepared from a mixture of 2-nitrohexane and 3-nitrohexane.

Example C

AOctM

A mixture (ratio of about 1 to 2 to 2) of 2-amino-2-methyl-1-octanol, 2-amino-2-ethyl-1-heptanol, and 2-amino-2-propyl-1-hexanol is prepared from a mixture of 2-nitrooctane, 3-nitrooctane and 4-nitrooctane

Example D

ACyPM 1-aminocyclopentylmethanol is prepared from nitro-cyclopentane

Example E

ACyOM 1-aminocyclooctylmethanol is prepared from nitro-cyclooctane

Example F

APP 2-amino-2-phenyl-1-propanol is prepared from 1-nitro-ethylbenzene

Example G

Evaluation of amino alcohols of the invention in metalworking fluids (MWFs) in comparison to 2-amino-2-methyl-1-propanol ("AMP"), without biocides. The semi-synthetic MWF formulations in Table 1 below are used for this example. Biocides are excluded in order to demonstrate that the amino alcohols of the invention are non-biocidal, and at most weakly inhibitory.

TABLE 1

| INGREDIENT | MANUFACTURER | AMP Comparative Example | ACyOM Example E | AOctM Example C | APP Example F | ACyHM Example A |
|---|---|---|---|---|---|---|
| Hydrocal 100 (lubricant) | Calumet Industries | 10.0% | 10.0% | 10.0% | 10.0% | 10.0% |
| Actrabase PS-470 (emulsifier) | Polartech | 14.0 | 14.0 | 14.0 | 14.0 | 14.0 |
| ALKATERGE T-IV | ANGUS Chemical | 4.0 | 4.0 | 4.0 | 4.0 | 4.0 |
| Xtol 304 (lubricant) | Polartech | 8.0 | 8.0 | 8.0 | 8.0 | 8.0 |
| Actrafos 110 (lubricant/emulsifier) | Polartech | 2.4 | 2.4 | 2.4 | 2.4 | 2.4 |
| Dowanol PnB (solvent) | Dow Chemical | 6.0 | 6.0 | 6.0 | 6.0 | 6.0 |
| Amino Alcohol | See previous section | 6.0 | 6.0 | 6.0 | 6.0 | 6.0 |
| Potassium Hydroxide (50% aqueous) | — | 0.30 | 1.20 | 1.05 | 1.90 | 1.90 |
| Igepal CO-630 (emulsifier) | Rhodia Corp. | 6.4 | 6.4 | 6.4 | 6.4 | 6.4 |
| Corfree M1 (corrosion inhibitor) | Invista Corp. | 2.0 | 2.0 | 2.0 | 2.0 | 2.0 |
| Deionized Water | — | 40.9 | 40.0 | 40.15 | 39.3 | 39.3 |
| Total | | 100 | 100 | 100 | 100 | 100 |

The above fluids are diluted to approximately 5% concentration with local tap water (from Lake Michigan). The approximate active amine concentration at dilution is 0.3%. The fluids are subjected to weekly microbial challenge using a mixed bacterial/fungal inoculum isolated from used MWFs, in accordance with ASTM E 2275. The bacterial and fungal counts are measured weekly using a serial dilution plate count method, and reported as colony forming units per milliliter (CFU/mL). The lower the CFU/mL the better the microbial control, and the longer the predicted service life of the fluid. A typical failure point is two consecutive weeks at 1×10E5 CFU/mL (or greater) bacteria and 1×10E3 CFU/mL (or greater) fungi.

Figure 1:
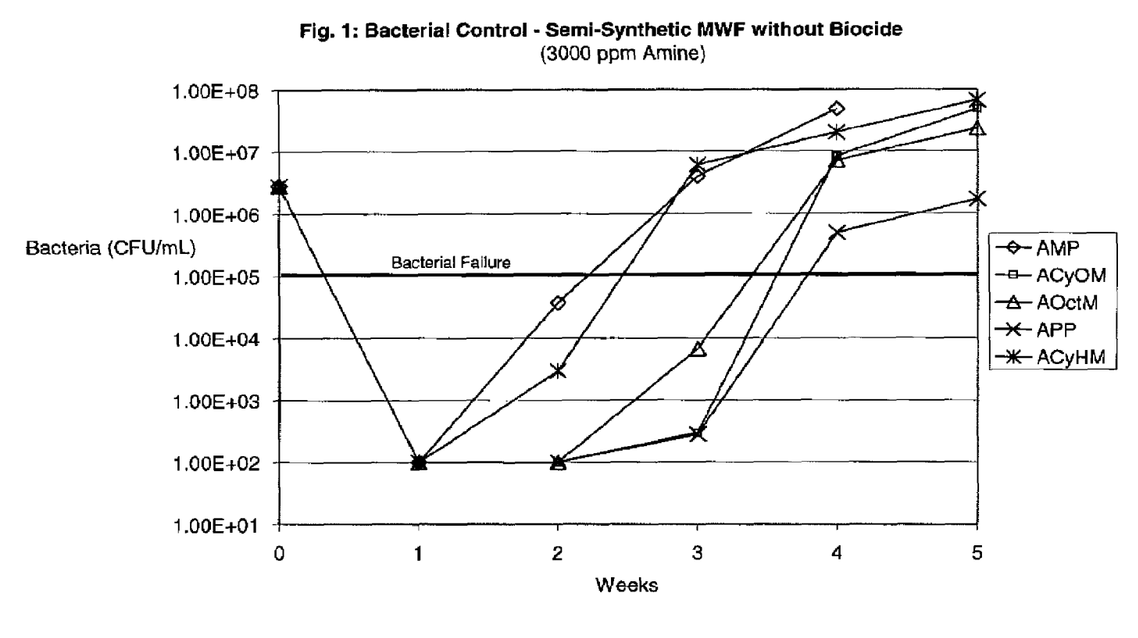
FIG. 1 is a graph showing the effect of amino alcohols of the invention, without biocides, against bacteria.
Figure 2:
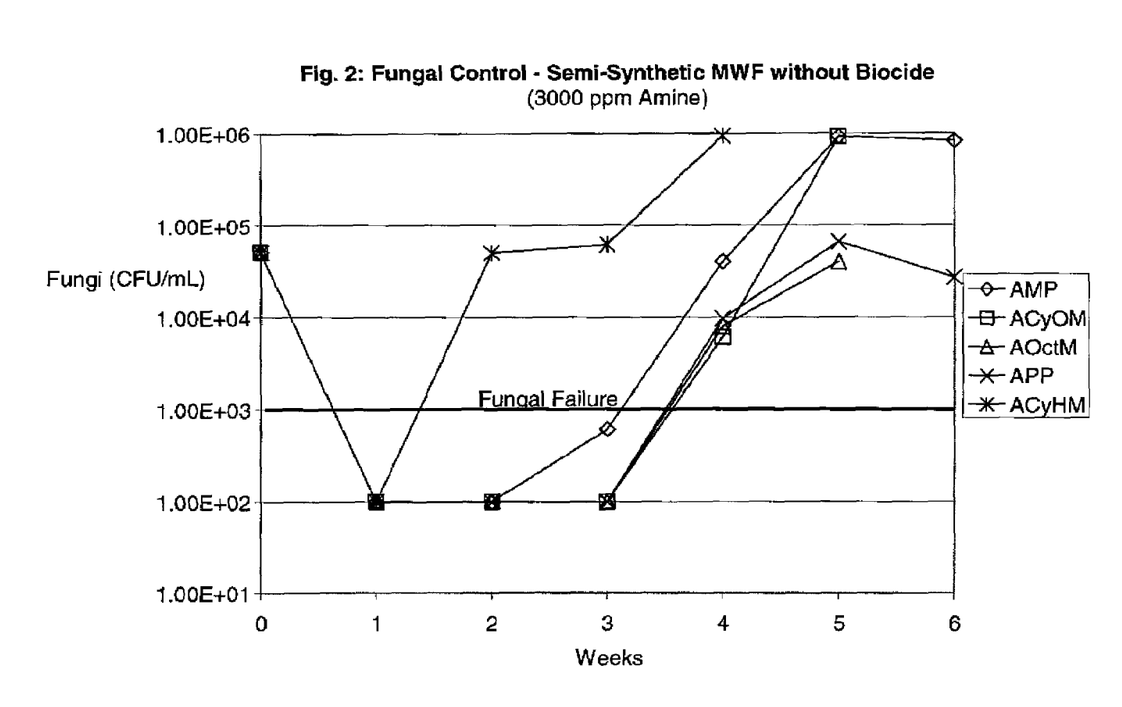
FIG. 2 is a graph showing the effect of amino alcohols of the invention, without biocides, against fungi.

Inspection of FIGS. 1 and 2 reveals that none of the amines of the present invention are significantly more inhibitory than the historically-used product AMP. None of them would be considered biocidal by those practiced in the art.

Example H

Evaluation of amino alcohols in MWFs in comparison to AMP, with triazine biocide.

Figure 3:
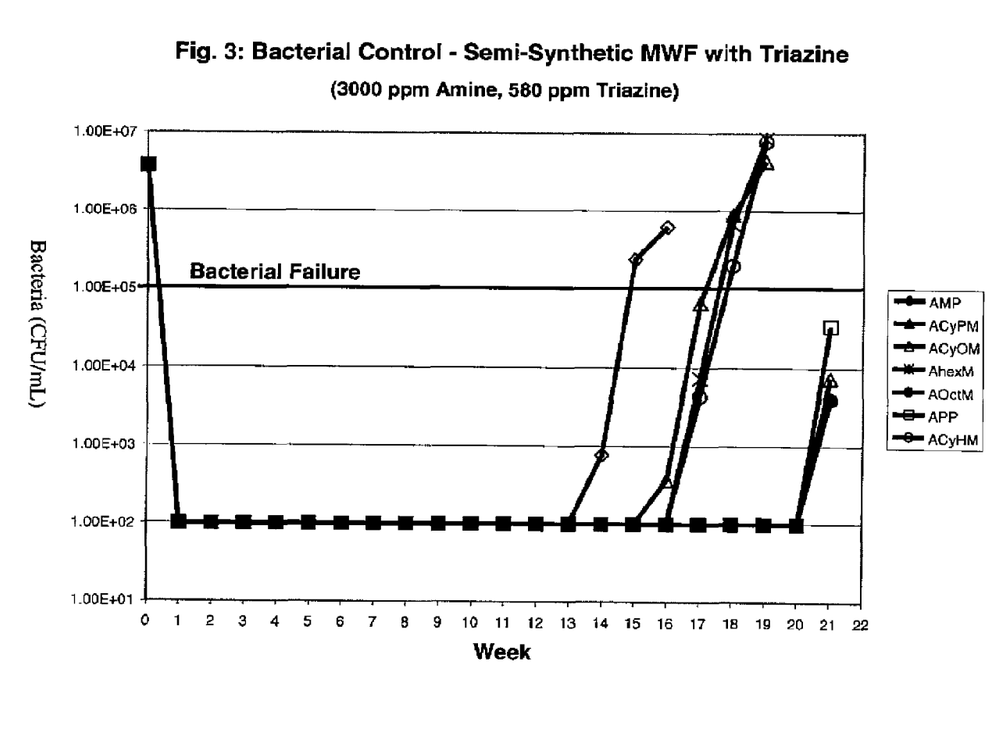
FIG. 3 is a graph showing bacterial growth data for metal working fluids containing comparative and inventive amino alcohols and triazine biocide.
Figure 4:
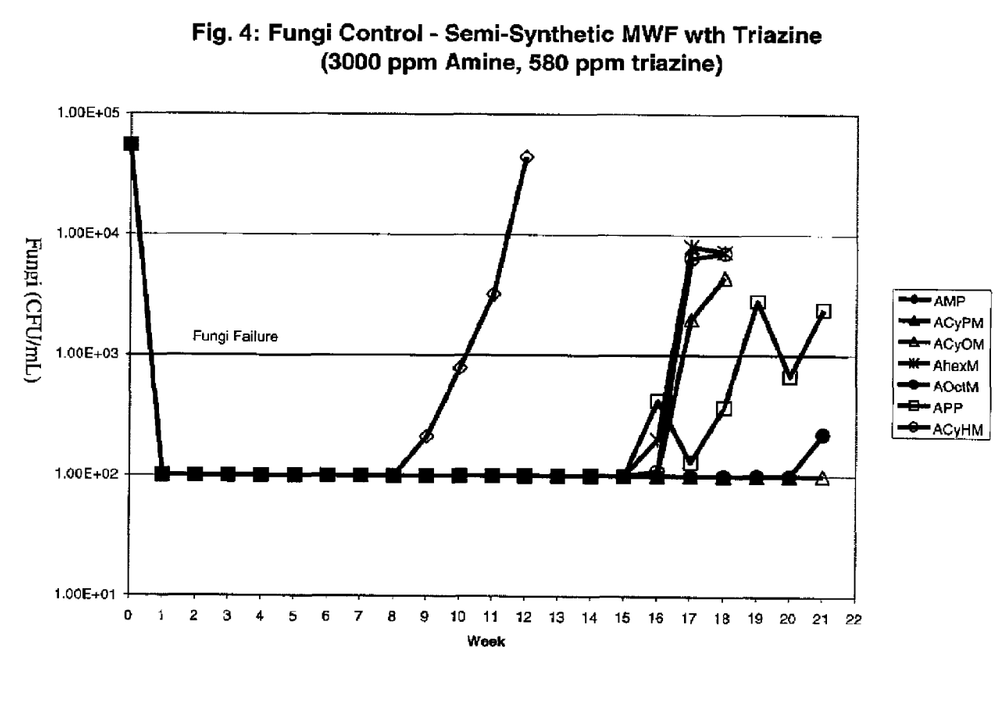
FIG. 4 is a graph showing fungal growth data for metal working fluids containing comparative and inventive amino alcohols and triazine biocide.

Identical formulations (Table 1) are prepared with each of the example amines (A, B, C, D, E, F) and compared to the control (AMP). Triadine 3 biocide from Arch Chemical (78% active triazine) is added to the fluid concentrates at 1.5%. The fluid concentrates are diluted at a rate of approximately 5% in Lake Michigan tap water; the active amino alcohol concentration at dilution is approximately 0.3% and the active triazine biocide dosage approximately 0.058%. These fluids are subjected to the same microbial challenge testing described in the previous example. The results for bacterial growth and fungal growth are described in FIGS. 3 and 4. Fluids containing several of the inventive compounds resist bacterial growth, but in particular fungal growth, significantly longer than those with the comparative AMP.

Example I

Evaluation of amino alcohols of the invention in comparison with AMP, with benzisothiazolinone biocide

Figure 5:
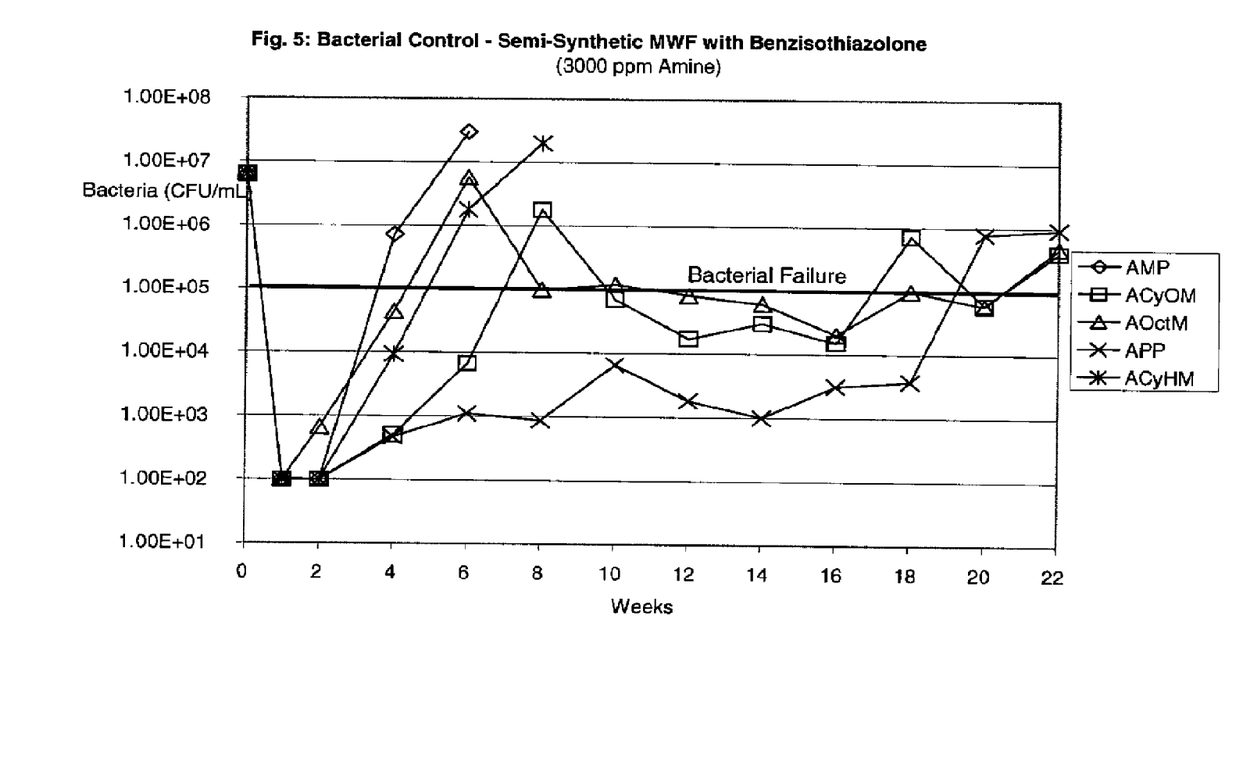
FIG. 5 is a graph showing bacterial growth data for metal working fluids containing comparative and inventive amino alcohols and benzisothiazolinone biocide.
Figure 6:
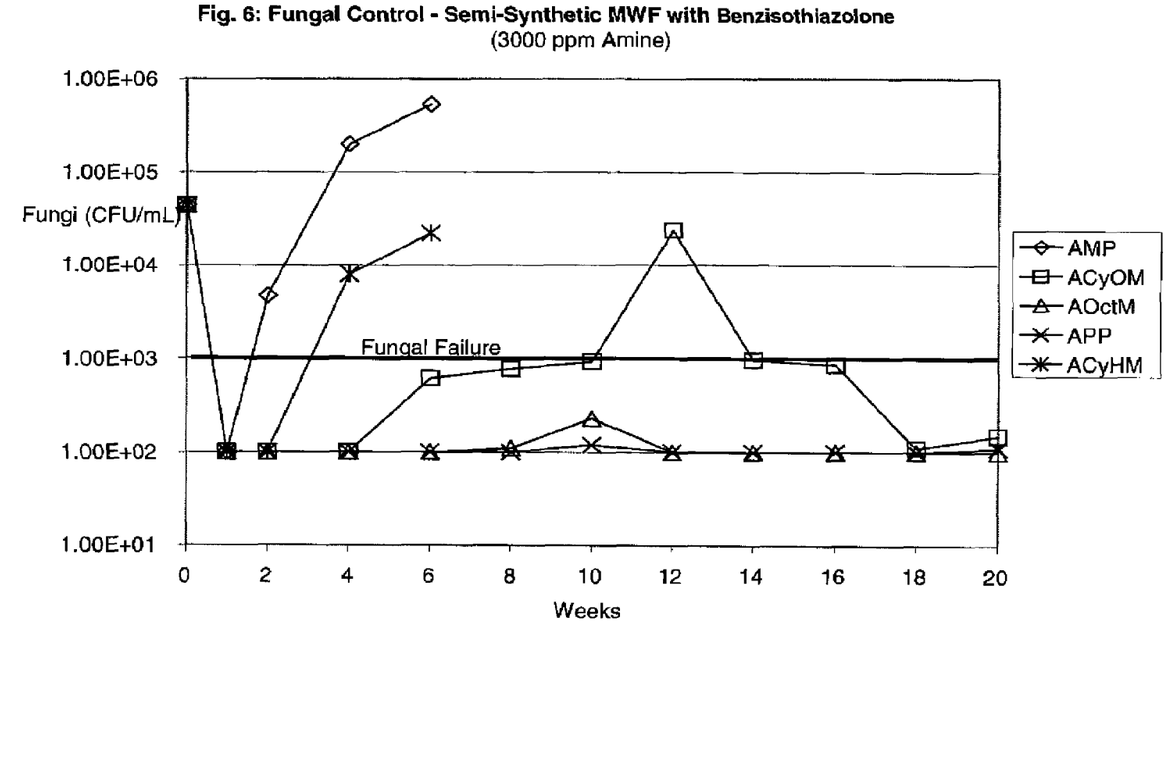
FIG. 6 is a graph showing fungal growth data for metal working fluids containing comparative and inventive amino alcohols and benzisothiazolinone biocide.

The base formulation in Table 1 is used to evaluate several of the amines of the invention (Examples A, C, E, F) in comparison with AMP, in combination with BIOBAN™ BIT 20. BIOBAN™ BIT 20 is supplied by the Dow Chemical Company and contains 20% active benzisothiazolinone (BIT). BIT is not known to be an effective biocide in MWFs, but is desirable because it is not made from formaldehyde and does not release formaldehyde during handling or use. BIOBAN™ BIT 20 is added at 1.8% to the fluid concentrate, providing approximately 0.018% active BIT at 5% dilution. Results of the microbial testing are described in FIGS. 5 and 6. The inventive compounds give significant improvements in the performance of BIT against both bacteria and fungi, relative to the fluid with AMP (comparative amino alcohol).

The invention has been described with reference to various specific and preferred embodiments and techniques. However, it should be understood that many variations and modifications may be made while remaining within the spirit and scope of the invention.

What is claimed is:

1. A biocidal composition comprising:
a biocidal agent that is 1,3,5-tris(2-hydroxyethyl)-s-triazine, 1,2-benzisothiazolin-3-one, 2-methyl-4-isothiazolin-3-one, octylisothiazolinone, dichloro-octylisothiazolinone, or dibromo-octylisothiazolinone; or a combination of 5-chloro-2-methyl-4-isothiazolin-3-one with 2-methyl-4-isothiazolin-3-one; and
a primary amino alcohol compound of the formula (II):

wherein
$R^2$, is linear or branched alkyl, or phenyl and $R^4$ is linear or branched alkyl, or $R^2$, $R^4$ and the carbon to which they are attached form a cycloalkyl ring, provided that $R^2$ and $R^4$ together contain 3 or more carbon atoms, and wherein the compound contains at least 6 carbon atoms and no more than 13 carbon atoms.

2. The composition of claim 1 further comprising one or more compounds selected from the group consisting of 2-amino-2-methyl-1-propanol, 2-amino-1-ethanol, 1-amino-2-propanol, bis(2-hydroxypropyl)amine, tris(2-hydroxypropyl)amine, bis(2-hydroxyethyl)amine, tris(2-hydroxyethyl) amine, 2-(2-aminoethoxy)ethanol, and 3-amino-4-octanol.

3. The composition of claim 1 wherein $R^2$ and $R^4$ together contain up to 11 carbon atoms.

4. The composition of claim 1 wherein $R^2$ and $R^4$ are each independently linear alkyl.

5. The composition of claim 1 wherein $R^2$ and $R^4$ together with the carbon to which they are attached form a cycloalkyl ring.

6. The composition of claim 1 wherein the amino alcohol is selected from (1-aminocyclohexyl)methanol, (1-aminocyclooctyl)methanol, 2-amino-2-phenyl-1-propanol, or (1-aminocyclopentyl)methanol, or the amino alcohol is a mixture of 2-amino-2-methyl-1-hexanol and 2-amino-2-ethyl-1-pentanol, or a mixture of 2-amino-2-methyl-1-octanol and 2-amino-2-ethyl-1-heptanol and 2-amino-2-propyl-1-hexanol.

7. A method of inhibiting the growth of microorganisms in an aqueous-based system comprising adding to said system an effective amount of a biocidal composition according to claim 1.

8. A method according to claim 7 wherein the aqueous-based system is a metal working fluid.

9. A metalworking fluid concentrate comprising a biocidal composition according to claim 1.

10. A metalworking fluid comprising a biocidal composition according to claim 1.

11. A metalworking fluid comprising water and a metalworking concentrate, wherein the metalworking concentrate comprises a biocidal composition according to claim 1.

12. A composition in which microbial growth is inhibited comprising: an aqueous based system; and a biocidal composition according to claim 1.

13. The composition according to claim 12 wherein the aqueous based system is latexes, water-based paints, water-based coatings, caulks, adhesives, tape joint compounds, mineral slurries, water-cooling systems, personal care products, soaps and detergents, disinfectants, cleaners, sanitizers, pesticide products, oilfield water, and water-based fluids used in oilfield applications such as drilling muds, fracturing fluids, and hydrotest fluids.

14. The composition according to claim 12 wherein the aqueous based system is a metal working fluid.

* * * * *